(12) United States Patent
Chang et al.

(10) Patent No.: US 8,974,794 B2
(45) Date of Patent: Mar. 10, 2015

(54) C(EPSILON)MX PEPTIDES FOR INDUCING IMMUNE RESPONSES TO HUMAN MIGE ON B LYMPHOCYTES

(71) Applicant: Academia Sinica, Taipei (TW)

(72) Inventors: Tse Wen Chang, Taipei (TW); Jiun-Bo Chen, Taipei (TW); Pheidias C. Wu, Bangiao (TW); Alfur F. Hung, Liouciou Township (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 14/254,453

(22) Filed: Apr. 16, 2014

(65) Prior Publication Data
US 2014/0220042 A1 Aug. 7, 2014

Related U.S. Application Data

(62) Division of application No. 13/888,913, filed on May 7, 2013, now Pat. No. 8,741,294, which is a division of application No. 13/203,483, filed as application No. PCT/CN2010/000232 on Feb. 25, 2010, now Pat. No. 8,460,664.

(60) Provisional application No. 61/155,224, filed on Feb. 25, 2009.

(51) Int. Cl.
*A61K 39/00* (2006.01)
*C07K 16/28* (2006.01)
*C07K 16/42* (2006.01)
*A61K 39/395* (2006.01)

(52) U.S. Cl.
CPC ......... *C07K 16/2803* (2013.01); *C07K 16/4291* (2013.01); *A61K 39/39566* (2013.01); *C07K 2316/95* (2013.01); *C07K 2317/24* (2013.01); *C07K 2317/56* (2013.01); *C07K 2317/565* (2013.01); *C07K 2317/34* (2013.01); *C07K 2317/73* (2013.01); *C07K 2317/732* (2013.01); *Y10S 424/805* (2013.01); *Y10S 424/81* (2013.01); *Y10S 530/862* (2013.01); *Y10S 530/868* (2013.01); *C07K 2317/30* (2013.01)
USPC .............. 424/185.1; 424/192.1; 424/193.1; 424/805; 424/810; 514/1.7; 530/862; 530/868

(58) Field of Classification Search
None
See application file for complete search history.

(56) References Cited

U.S. PATENT DOCUMENTS

| 5,079,344 | A | 1/1992 | Chang et al. |
|---|---|---|---|
| 5,089,603 | A | 2/1992 | Chang |
| 5,091,313 | A | 2/1992 | Chang |
| 5,231,026 | A | 7/1993 | Chang |
| 5,252,467 | A | 10/1993 | Chang |
| 5,254,671 | A | 10/1993 | Chang |
| 5,260,416 | A | 11/1993 | Chang |
| 5,274,075 | A | 12/1993 | Chang |
| 5,281,699 | A | 1/1994 | Chang |
| 5,292,867 | A | 3/1994 | Chang |
| 5,298,420 | A | 3/1994 | Chang |
| 5,310,875 | A | 5/1994 | Chang |
| 5,342,924 | A | 8/1994 | Chang |
| 5,362,643 | A | 11/1994 | Chang |
| 5,420,251 | A | 5/1995 | Chang et al. |
| 5,422,258 | A | 6/1995 | Chang |
| 5,449,760 | A | 9/1995 | Chang |
| 5,484,907 | A | 1/1996 | Chang et al. |
| 5,514,776 | A | 5/1996 | Chang |
| 5,543,144 | A | 8/1996 | Chang |
| 5,601,821 | A * | 2/1997 | Stanworth et al. ......... 424/139.1 |
| 5,614,611 | A | 3/1997 | Chang |
| 5,653,980 | A * | 8/1997 | Hellman .................... 424/184.1 |
| 5,690,934 | A | 11/1997 | Chang et al. |
| 5,866,129 | A | 2/1999 | Chang et al. |
| 6,887,472 | B2 * | 5/2005 | Morsey et al. ............. 424/134.1 |
| 7,897,151 | B2 * | 3/2011 | Morsey et al. ............. 424/185.1 |
| 8,071,097 | B2 | 12/2011 | Wu et al. |
| 8,137,670 | B2 | 3/2012 | Wu et al. |
| 8,460,664 | B2 | 6/2013 | Chang et al. |
| 8,741,294 | B2 | 6/2014 | Chang et al. |
| 2009/0010924 | A1 | 1/2009 | Wu et al. |
| 2009/0220416 | A1 | 9/2009 | Welt et al. |

FOREIGN PATENT DOCUMENTS

| KR | 10-2012-0019429 A | 3/2012 |
|---|---|---|
| WO | WO 89/06138 A1 | 7/1989 |
| WO | WO 90/15614 A1 | 12/1990 |
| WO | WO 91/04055 A1 | 4/1991 |
| WO | WO 91/11456 A1 | 8/1991 |
| WO | WO 92/07574 A1 | 5/1992 |
| WO | WO 96/12740 A1 | 5/1996 |
| WO | WO 9612740 A1 * | 5/1996 |
| WO | WO 98/53843 A1 | 12/1998 |
| WO | WO 2007/041171 A2 | 4/2007 |
| WO | WO 2007/131129 A2 | 11/2007 |
| WO | WO 2008/116149 A2 | 9/2008 |
| WO | WO 2010/097012 A1 | 9/2010 |
| WO | WO 2011/108008 A2 | 9/2011 |

OTHER PUBLICATIONS

Disis et al., Blood. Jul. 1, 1996;88(1):202-10.*

(Continued)

*Primary Examiner* — Michael Szperka
(74) *Attorney, Agent, or Firm* — Wolf, Greenfield & Sacks, P.C.

(57) ABSTRACT

The invention pertains to methods of using CεmX peptides (e.g., GLAGGSAQSQRAPDRVL; SEQ ID NO:2) that can bind effectively induce immune responses to membrane-bound IgE (mIgE) expressed on the surface of human B lymphocytes.

15 Claims, 10 Drawing Sheets

(56) References Cited

OTHER PUBLICATIONS

Kass et al., Cancer Res. Feb. 1, 1999;59(3):676-83.*
Timmerman et al., J Immunol. May 1, 2000;164(9):4797-803.*
[No Author Listed] Rituxan® (Rituximab) Proposed Mechanism of Action. Last accessed from http://www.rituxan.com/hem/hcp/mechanism-action/index.html on Oct. 5, 2012.
Achatz et al., Membrane bound IgE: the key receptor to restrict high IgE levels. Open Immunology Journal. 2008;1:25-32.
Batista et al., Characterization and expression of alternatively spliced IgE heavy chain transcripts produced by peripheral blood lymphocytes. J Immunol. Jan. 1, 1995;154(1):209-18.
Batista et al., Characterization of the human immunoglobulin epsilon mRNAs and their polyadenylation sites. Nucleic Acids Res. Dec. 11, 1995;23(23):4805-11.
Batista et al., The two membrane isoforms of human IgE assemble into functionally distinct B cell antigen receptors. J Exp Med. Dec. 1, 1996;184(6):2197-205.
Benhamou et al., Anti-immunoglobulins induce death by apoptosis in WEHI-231 B lymphoma cells. Eur J Immunol. Jun. 1990;20(6):1405-7.
Berard et al., Activation sensitizes human memory B cells to B-cell receptor-induced apoptosis. Immunology. Sep. 1999;98(1):47-54.
Bozelka et al., IgE isotype suppression in anti-epsilon-treated mice. Immunology. Jul. 1982;46(3):527-32.
Brightbill et al., Antibodies specific for a segment of human membrane IgE deplete IgE-producing B cells in humanized mice. J Clin Invest. Jun. 2010;120(6):2218-29.
Caraux et al., Surface immunoglobulins as targets for anti-immunoglobulin-dependent cell-mediated lysis of B cells. Cell Immunol. Mar. 1983;76(2):372-8.
Chan et al., The novel human IgE epsilon heavy chain, epsilon tailpiece, is present in plasma as part of a covalent complex. Mol Immunol. Apr. 2000;37(5):241-52.
Chang et al., Anti-IgE antibodies for the treatment of IgE-mediated allergic diseases. Adv Immunol. 2007;93:63-119.
Chang et al., Monoclonal antibodies specific for human IgE-producing B cells: a potential therapeutic for IgE-mediated allergic diseases. Biotechnology (N Y). Feb. 1990;8(2):122-6.
Chang, Developing antibodies for targeting immunoglobulin and membrane-bound immunoglobulin E. Allergy Asthma Proc. Mar.-Apr. 2006;27(2 Suppl 1):S7-14.
Chang, The pharmacological basis of anti-IgE therapy. Nat Biotechnol. Feb. 2000;18(2):157-62.
Chen et al., Controlling IgE production by targeting membrane-bound IgE on B Cells. Jun. 19, 1991. Chapter s 1-4. 76 pages.
Chen et al., Monoclonal antibodies against the C(epsilon)mX domain of human membrane-bound IgE and their potential use for targeting IgE-expressing B cells. Int Arch Allergy Immunol. Aug. 2002;128(4):315-24.
Chen et al., Unique epitopes on C epsilon mX in IgE-B cell receptors are potentially applicable for targeting IgE-committed B cells. J Immunol. Feb. 15, 2010;184(4):1748-56. Epub Jan. 18, 2010.
Chinn et al., Antibody therapy of non-Hodgkin's B-cell lymphoma. Cancer Immunol Immunother. May 2003;52(5):257-80. Epub Feb. 28, 2003.
Chowdhury et al., Targeting the junction of CεmX and ε-migis for the specific depletion of mIgE-expressing B cells. Mol Immunol. Oct. 2012;52(3-4):279-88. Epub Jun. 29, 2012.
Davis et al., An epitope on membrane-bound but not secreted IgE: implications in isotype-specific regulation. Biotechnology (N Y). Jan. 1991;9(1):53-6.
Davis et al., Can anti-IgE be used to treat allergy? Springer Semin Immunopathol. 1993;15(1):51-73.
Donjerković et al., Activation-induced cell death in B lymphocytes. Cell Res. Sep. 2000;10(3): 179-92.
Eray et al., Cross-linking of surface IgG induces apoptosis in a bcl-2 expressing human follicular lymphoma line of mature B cell phenotype. Int Immunol. Dec. 1994;6(12):1817-27.
Feichtner et al., Targeting the extracellular membrane-proximal domain of membrane-bound IgE by passive immunization blocks IgE synthesis in vivo. J Immunol. Apr. 15, 2008;180(8):5499-505.

Grafton et al., Mechanisms of antigen receptor-dependent apoptosis of human B lymphoma cells probed with a panel of 27 monoclonal antibodies. Cell Immunol. Nov. 25, 1997;182(1):45-56.
Haak-Frendscho et al., Administration of an anti-IgE antibody inhibits CD23 expression and IgE production in vivo. Immunology. Jun. 1994;82(2):306-13.
Haba et al., Inhibition of IgE synthesis by anti-IgE: role in long-term inhibition of IgE synthesis by neonatally administered soluble IgE. Proc Natl Acad Sci U S A. May 1990;87(9):3363-7.
Hung et al., Alleles and isoforms of human membrane-bound IgA1. Mol Immunol. Aug. 2008;45(13):3624-30. Epub Jun. 6, 2008.
Inführ et al., Molecular and cellular targets of anti-IgE antibodies. Allergy. Aug. 2005;60(8):977-85.
Janeway et al., Immunobiology: the immune system in health and disease. $6^{th}$ edition. 2005:352-353, 401-402.
Lin et al., CεmX peptide-carrying HBcAg virus-like particles induced antibodies that down-regulate mIgE-B lymphocytes. Mol Immunol. Oct. 2012;52(3-4):190-9.
Lorenzi et al., Sequence-specific antibodies against human IgE isoforms induced by an epitope display system. Immunotechnology. Mar. 1999;4(3-4):267-72.
Major et al., Structural features of the extracellular portion of membrane-anchoring peptides on membrane-bound immunoglobulins. Mol Immunol. Feb. 1996;33(2):179-87.
Martin et al., B cell immunobiology in disease: evolving concepts from the clinic. Annu Rev Immunol. 2006;24:467-96.
Mathas et al., Anti-CD20- and B-cell receptor-mediated apoptosis: evidence for shared intracellular signaling pathways. Cancer Res. Dec. 15, 2000;60(24):7170-6.
Parry et al., Hypercross-linking surface IgM or IgD receptors on mature B cells induces apoptosis that is reversed by costimulation with IL-4 and anti-CD40. J Immunol. Mar. 15, 1994;152(6):2821-9.
Peng et al., A new isoform of human membrane-bound IgE. J Immunol. Jan. 1, 1992;148(1):129-36.
Poggianella et al., The extracellular membrane-proximal domain of human membrane IgE controls apoptotic signaling of the B cell receptor in the mature B cell line A20. J Immunol. Sep. 15, 2006;177(6):3597-605.
Takamuku et al., Apoptosis in antibody-dependent monocyte-mediated cytotoxicity with monoclonal antibody 17-1A against human colorectal carcinoma cells: enhancement with interferon gamma. Cancer Immunol Immunother. Dec. 1996;43(4):220-5.
Talay et al., IgE$^+$ memory B cells and plasma cells generated through a germinal-center pathway. Nat Immunol. Feb. 26, 2012;13(4):396-404.
Wan et al., Genetic variations in the C epsilon mX domain of human membrane-bound IgE. Immunogenetics. May 2010;62(5):273-80. Epub Mar. 24, 2010.
Yu et al., Two isoforms of human membrane-bound alpha Ig resulting from alternative mRNA splicing in the membrane segment. J Immunol. Dec. 1, 1990;145(11):3932-6.
Zhang et al., Complex alternative RNA splicing of epsilon-immunoglobulin transcripts produces mRNAs encoding four potential secreted protein isoforms. J Biol Chem. Jan. 7, 1994;269(1):456-62.
Zhang et al., Two unusual forms of human immunoglobulin E encoded by alternative RNA splicing of epsilon heavy chain membrane exons. J Exp Med. Jul. 1, 1992;176(1):233-43.
GenBank Submission; NIH/NCBI, Accession No. AER46505.1, Kuwata, Nov. 6, 2011, 2 pages.
GenBank Submission; NIH/NCBI, Accession No. BAE71466.1, Furukawa et al., Jan. 6, 2006, 2 pages.
GenBank Submission; NIH/NCBI, Accession No. S17626, Clackson et al., Jan. 21, 2000, 2 pages.
GenBank Submission; NIH/NCBI, Accession No. S45714, Kim et al., May 7, 1999, 3 pages.
Lyczak et al., Expression of novel secreted isoforms of human immunoglobulin E proteins. J Biol Chem. Feb. 16, 1996;271(7):3428-36.
MacGlashan, IgE-dependent signaling as a therapeutic target for allergies, Trends in Pharmacological Sciences, 2012, vol. 33, No. 9, pp. 502-209.
Wagner et al., Monoclonal anti-equine IgE antibodies with specificity for different epitopes on the immunoglobulin heavy chain of native IgE, Veterinary Immunology and Immunopathology, 2003, vol. 92, No. 1, pp. 45-60.

* cited by examiner

FIG. 1

```
         CH4                                              CεmX                                    migis
         SVNPGLAGGSAQSQRAPDRVLCHSGQQQGLPRAAGGSVPHPRCHCGAGRADWPGPPELDV P1       SVNPGLAGGSAQSQRAPDRVL
P2                              HSGQQQGLPRAAGGSVPHPR
P3                                                      GAGRADWPGPPELDV
```

| | 5H2 | mIgG | a20 | 1G2 | 3A6 | 3H11 | 6H12 | 18A11 | 1A8 | 4B12 | 23B8 | 26H2 |
|---|---|---|---|---|---|---|---|---|---|---|---|---|
| P1 | – | – | – | – | – | – | – | – | – | + | – | – |
| P2 | – | – | – | – | – | – | – | – | – | – | – | + |
| P3 | – | – | + | + | + | + | + | + | + | – | + | – |
| mIgE.FcL | + | – | + | + | + | + | + | + | + | + | + | + |
| mIgE.Fcs | + | – | – | – | – | – | – | – | – | – | – | – |
| IgE | + | – | – | – | – | – | – | – | – | – | – | – |

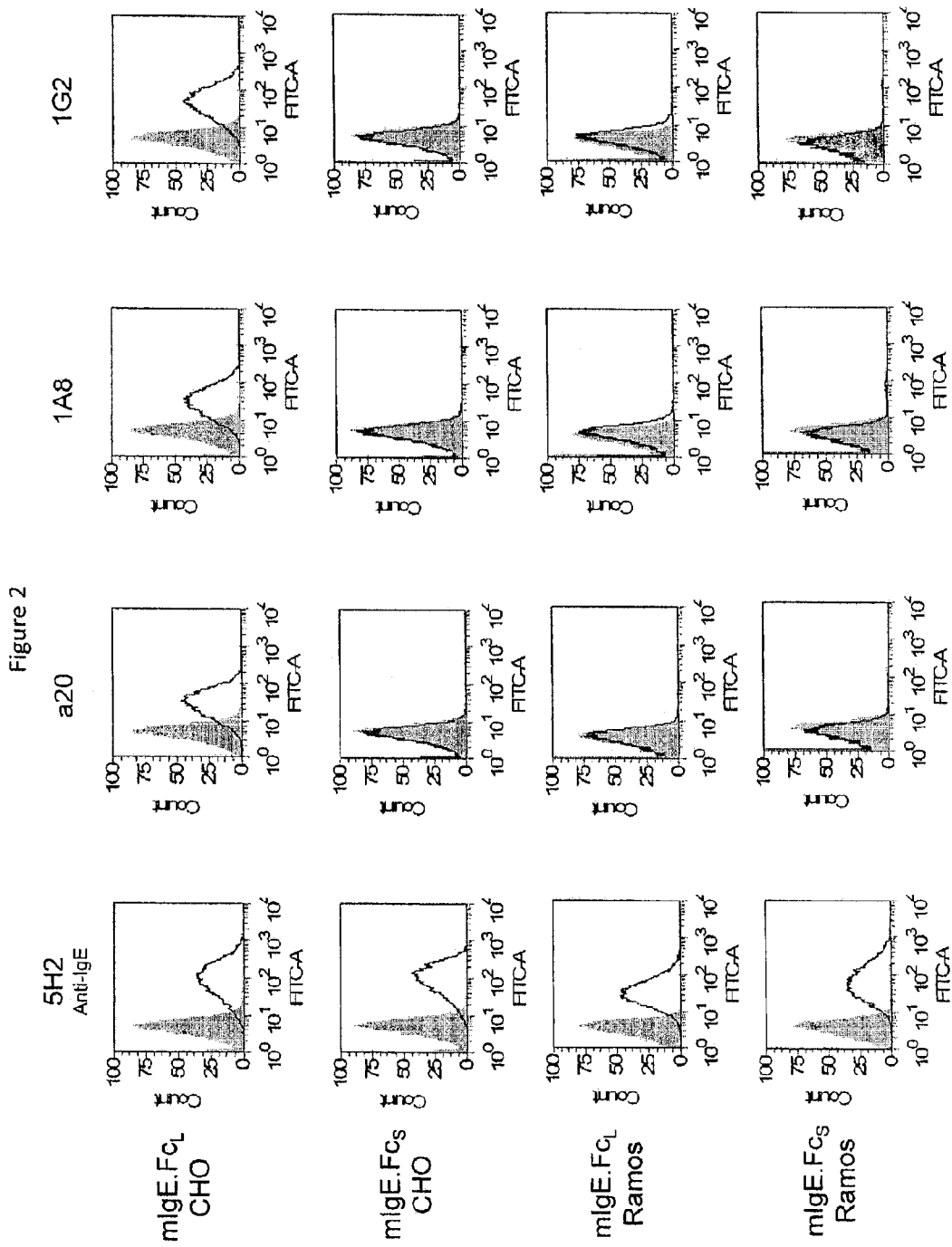

```
Light chain
           1      .    10    .    20    .   abcde 30     .     40     .     50     .    60
4B12       DVLMTQTPLSLPVSLGDQASISCRSSQSIVHSNGNTYLEWYLQKPGQSPKLLIYKVSNRFSGVPD
KV2        DIVMTQTPLSLSVTPGQPASISCKSSQSLLHSDGKTYLYWYLQKPGQSPQLLIYEVSSRFSGVPD
Replace     IV              S TP QP                                      Q
                   .  70      .   80    .    90     .   100
4B12       RFSGSGSGTDFTFKISRVEAEDLGVYYCFQGSHVPPTFGGGTKLEIKR
KV2        RFSGSGSGTDFTLKISRVEAEDVGVYYCMQGIQLPPTFGGGTKVEIKR
Replace                 L           V           V Heavy chain
           1      .    10    .    20    .    30    .a   40    .     50    .     60      .
4B12       DVQLQESGPGLVKPSQSLSLTCTVTGYSITSDYAWNWIRQFPGNKLEWMGSISYSGITGYNPSLKS
HV4        QVQLQESGPGLVKPSETLSLTCTVSGYSISSGYYWGWIRQPPGKGLEWIGSIYHSGSTYYNPSLKS
Replace    Q               ET        S              P  KG    I
                .  70      .   80  abc    .    90     .   100    .   110
4B12       RISVTRDTSKNQFFLQLNSVTTEDTATYYCARMGYDGLAYWGHGTTVTVSA
HV4        RVTISVDTSKNQFSLKLSSVTAADTAVYYCAR-------YWGQGTLVTVSS
Replace     VTISV        SKS     AA  V              Q L    S
```

FIG. 5

C(EPSILON)MX PEPTIDES FOR INDUCING IMMUNE RESPONSES TO HUMAN MIGE ON B LYMPHOCYTES

CROSS-REFERENCE TO RELATED APPLICATIONS

This application is a divisional of U.S. application Ser. No. 13/888,913, which is a divisional of U.S. application Ser. No. 13/203,483, filed on Nov. 9, 2011, now U.S. Pat. No. 8,460,664, which is a US National Stage entry from international application PCT/CN2010/000232 filed Feb. 25, 2010, which claims priority to U.S. provisional patent application Ser. No. 61/155,224 filed Feb. 25, 2009. The content of each of the prior applications is incorporated by reference herein in its entirety.

BACKGROUND OF THE INVENTION

IgE plays a central role in mediating type I hypersensitivity reactions that are responsible for causing allergic diseases, including allergic asthma, allergic rhinitis, atopic dermatitis, and others. Allergic reactions are the responses of the immune system toward harmless environmental substances, such as dust mites, tree and grass pollens, certain food and drugs, and bee and fire ant bites. In such reactions, the binding of an allergen to IgE on the surface of basophils and mast cells causes the cross-linking of IgE and the aggregation of the underlying receptors of IgE.Fc, the type I IgE.Fc receptors, or FcεRI. This receptor aggregation subsequently activates the signaling pathway leading to the exocytosis of granules and the release of pharmacologic mediators, such as histamine, leukotrienes, tryptase, cytokines and chemokines. The release of those mediators from mast cells and basophils causes the various pathological manifestations of allergy.

Anti-IgE antibodies that bind to free IgE in the blood and in interstitial fluid and to mIgE on B cells, but not to IgE bound by FcεRI on basophils and mast cells, have been developed for treating IgE-mediated allergic diseases. The treatment with a humanized anti-IgE antibody, omalizumab (trade name Xolair), has shown multiple pharmacologic effects in attenuating type I hypersensitivity in various allergic indications. The antibody binds to IgE with high affinity at a site in the CH3 domain of Fc that overlaps with the binding site of FcεRI. Hence, the therapy is based on the binding of the antibody to free IgE and to mIgE on B lymphoblasts and on memory B cells, which leads to the reduction of overall free IgE level in blood and interstitial fluid.

The binding of anti-IgE to free IgE further prevents IgE binding to FcεRI on the surface of basophils and mast cells. As the FcεRI unoccupied by IgE is unstable and subsequently internalized and degraded, the depletion of free IgE with anti-IgE binding also gradually down-regulates FcεRI on basophils and mast cells. Evidence for other effects of the antibody therapy has been found, including the neutralization of cytokinergic activities, the attenuation of overall inflammatory activity, and possibly the sweeping of allergens through the accumulation of IgE-anti-IgE immune complexes.

One of the inventors (T. W. Chang) of this invention discovered that in addition to the antigenic site on CH3 of IgE that omalizumab binds to, another antigenic site, referred to as CεmX, exists on human mIgE for the targeting of mIgE-expressing B lymphocytes. CεmX is a 52-amino acid segment located between the CH4 domain and the C-terminal membrane-anchoring segment of human membrane-bound ε chain (mε). It has been shown that in most human subjects studied, the mε without CεmX ($m\epsilon_S$) accounts for minute proportions, whereas mε chain with CεmX ($m\epsilon_L$) is dominantly expressed. The mRNAs for ε chain of free, secreted IgE and for $m\epsilon_S$ and $m\epsilon_L$ of mIgE are all derived from alternative splicing of the ε RNA transcript. The amino acid and nucleotide sequences of CεmX are unique in the entire protein and DNA databases. Therefore, CεmX provides a unique antigenic site for targeting mIgE and the mIgE-expressing B cells.

The research group of Chang previously reported the development of several CεmX-specific mouse monoclonal antibodies, including a20, which can bind to recombinant proteins containing CεmX segment and to cells of SKO-007 cell line, which was a human myeloma-derived cell line expressing human mIgE, and to cells of a CHO cell line, which was transfected with the gene corresponding to the segment from CH2 domain through the cytoplasmic end of $m\epsilon_L$ ($m\epsilon_{L(CH2-CM)}$; CM: cytoplasm). The monoclonal antibody a20 and all antibodies developed earlier were found to bind to an 8-a. a. peptidic region, RADWPGPP (SEQ ID NO:1), residues #45-52, at the C-terminal end of the 52 aa CεmX domain.

SUMMARY OF THE INVENTION

This invention pertains to the development and identification of antibodies that are specific for CεmX domain of human mIgE and that can bind to mIgE on human B lymphocytes. It also pertains to the utility of these antibodies in treating allergic and other diseases that are mediated by IgE.

In studying the anti-CεmX monoclonal antibody a20, which was developed by the research group of Chang, it was found that a20 has good binding to $m\epsilon_{L(CH2-CM)}$ gene-transfected cell lines, such as CHO cell line or NS0 cell line, that do not express Igα (CD79a), Igβ (CD79b), CD21, CD19, CD81, and other proteins associated with B cell receptor (BCR). However, a 20 was found to bind poorly to $m\epsilon_{L(CH2-CM)}$ gene-transfected cell lines that express Igα, Igβ, and other BCR-associated proteins, such as Ramos cell line. We hypothesized that the antigenic epitope on CεmX recognized by a20 may be blocked by certain BCR-associated protein(s). Therefore, a20 monoclonal antibody and its chimeric or humanized versions would not be suitable for use in human patients in vivo for the purpose of targeting mIgE expressing B lymphoblasts and memory cells.

If the peptidic epitope, RADWPGPP (SEQ ID NO:1), is the only epitope for inducing antibody response, monoclonal antibodies generated from hybridoma methodology using mice that are immunized with human CεmX-containing proteins would all be specific for this peptide region. However, if this epitope is a dominant epitope, but not the only immunogenic epitope, monoclonal antibodies specific for other antigenic epitopes on CεmX could still be developed. It is possible that there exists an epitope(s) on CεmX that is not blocked by BCR-associated proteins for antibody binding. If so, an antibody that binds to IgE on B cells and that can be used for targeting those B cells may still be developed.

In the following examples, we have successfully shown that although RADWPGPP (SEQ ID NO:1) is a dominant epitope, it is not the only immunogenic and antigenic epitope on CεmX. Furthermore, we have discovered monoclonal antibodies, 4B 12 and 26H2, that bind to CεmX on antigenic epitopes not located in the region of RADWPGPP (SEQ ID NO:1). Those monoclonal antibodies do not compete with a20 antibody in binding to CεmX. They bind to mIgE on B cells much more strongly than a 20 and are much more effective than a20 in causing antibody-dependent cytolysis and apoptosis of mIgE-expressing cells.

The examples indicate that monoclonal antibodies, such as 4B12 and 26H2, can bind to mIgE on human B lymphocytes and are suitable for use to target mIgE-expressing B lymphoblasts and memory B cells for the down-regulation of IgE synthesis. The antibodies in chimeric or humanized forms will be useful for use in patients affected with IgE-mediated allergic diseases, such as allergic asthma, allergic rhinitis, and atopic dermatitis. Since neutralization of IgE by anti-IgE has been shown to effectively treat cold-induced urticaria, chronic urticaria, cholinergic urticaria, chronic rhinosinusitis, systemic mastocytosis, cutaneous mastocytosis, allergic bronchopulmonary aspergillosis, recurrent idiopathic angioedema, and interstitial cystitis, or eosinophil-associated gastrointestinal disorders, antibodies, such as 4B 12 and 26H2, may also be applied to treat those various diseases.

The examples further suggest the potential utility of the peptides recognized by 4B12 and 26H2 in inducing immune response against CεmX and hence mIgE-expressing B cells. The peptides and their analogues with similar antigenic properties, i.e., with binding activity to anti-CεmX antibodies, such as 4B 12 and 26H2, may be used individually or in combination in molecular constructs that also contain moieties that can induce T-cell help. Such constructs can induce active immunization against mIgE-expressing B cells and thus achieving the effects of down-regulating total IgE synthesis.

One aspect of the present disclosure features a CεmX-specific antibody capable of binding to membrane-bound IgE on human B lymphocytes and incapable of binding to RADWPGPP (SEQ ID NO:1) peptide. In one example, such a CεmX-specific antibody can be a mouse monoclonal antibody. In another example, the antibody is a chimeric antibody comprising the variable regions of a mouse monoclonal antibody and constant regions of human antibodies. Alternatively, the antibody is a humanized monoclonal antibody comprising essentially the hypervariable regions of a mouse monoclonal antibody and the framework regions and constant regions of human antibodies. In yet another example, the antibody is a human antibody.

Another aspect of the present disclosure features fragment of the CεmX-specific antibody described above, the antibody fragment being capable of binding to membrane-bound IgE on human B lymphocytes and incapable of binding to RAD-WPGPP peptide (SEQ ID NO:1). Such an antibody fragment can be Fab, F(ab')$_2$, or single-chain Fv.

In another aspect, the present disclosure provides a therapeutic method of using any of the antibodies described herein to treat IgE-mediated diseases, which can be allergic asthma, allergic rhinitis, or atopic dermatitis. In some embodiments, the IgE-mediated disease is cold-induced urticaria, chronic urticaria, cholinergic urticaria, chronic rhinosinusitis, systemic mastocytosis, cutaneous mastocytosis, allergic bronchopulmonary aspergillosis, recurrent idiopathic angioedema, and interstitial cystitis, or eosinophil-associated gastrointestinal disorders.

In some embodiments, the antibody described herein binds GLAGGSAQSQRAPDRVL (SEQ ID NO:2) or an analogue with similar antigenic property. In other embodiments, the antibody binds to HSGQQQGLPRAAGGSVPHPR (SEQ ID NO:3) or an analogue with similar antigenic property.

Also within the scope of this disclosure are (i) a therapeutic method of inducing immune response in patients in vivo by employing an immunogen containing GLAGGSAQSQRAPDRVL (SEQ ID NO:2) or an analogue with similar antigenic property, (ii) a therapeutic method of inducing immune response in patients in vivo by employing an immunogen containing HSGQQQGLPRAAGGSVPHPR (SEQ ID NO:3) or an analogue with similar antigenic property, and (iii) a therapeutic method of inducing immune response in patients in vivo by employing an immunogen containing GLAGGSAQSQRAPDRVL (SEQ ID NO:2) or an analogue with similar antigenic property and HSGQQQGL-PRAAGGSVPHPR (SEQ ID NO:3) or an analogue with similar antigenic property

EXAMPLE 1

New Anti-CεmX Monoclonal Antibodies Binding to Antigenic Sites Other than RADWPGPP (SEQ ID NO:1)

To induce anti-CεmX immune response, BALB/c mice were immunized twice subcutaneously with 50 μg of n-un-decyl-β-d-maltopyranoside (UDM; Anatrace)-solublized mIgE.Fc$_L$ recombinant proteins that were emulsified in Titer-Max Gold adjuvant (Sigma-Aldrich) according manufacturer's suggestions at 2 week intervals. We avoided hyper-immunization protocol, so that the mice would not produce antibodies only toward the dominant RADWPGPP epitope. A final boost was given intraperitoneally with 0.1 mg of UDM-solublized mIgE.Fc$_L$ recombinant proteins without adjuvant. One day before fusion, NS0 cells were reseeded in fresh DMEM medium (Invitrogen) supplemented with 10% heat-inactivated fetal bovine serum (FBS; Invitrogen), and 1% penicillin-streptomycin mixture (100× Pen-Strep solution; Invitrogen) at a cell density of 5×10$^5$ cells/ml. Three days after the final boost, the spleen cells from two immunized mice were harvested and washed with serum-free DMEM medium twice. 5×10$^7$ NS0 cells were harvested and washed with serum-free DMEM medium twice. After washing, spleen cells and NS0 cells were fused by adding 1 ml of pre-warmed 50% polyethyleneglycerol 1500 (PEG 1500, Roche Applied Science) while continually stirring cells gently with the pipette tip over 1 min, stirring cells for further 1 min, adding 2 ml pre-warmed serum-free DMEM over 2 min, and finally adding 8 ml serum-free DMEM over 2 min. After centrifugation at 200×g for 10 min, fused cells were resuspended with 600 ml of HAT medium [DMEM medium supplemented with 2% hypoxanthine-aminopterin-thymidine mixture (50× HAT solution; Invitrogen), 10% BM-Condimed H1 (Roche Applied Science), 10% heat-inactivated FBS, and 1% penicillin-streptomycin mixture] and distributed into 30 96-well culture plates at 200 μl/well. On days 3, 100 μl of HAT medium was added to each well. On days 7 and 10, medium was freshened by aspiring half the volume of each well and replacing with HAT medium. On days 14, hybridoma supernatants were used to screen anti-CεmX mAbs for binding to UDM-solublized mIgE.Fc$_L$ or mIgE.Fc$_S$ proteins by enzyme-linked immunosorbent assay (ELISA).

To screen hybridomas secreting anti-C☐mX mAbs by ELISA, purified UDM-solublized mIgE.Fc$_L$ or mIgE.Fc$_S$ proteins were coated on 96-well MaxiSorp plates (Nunc) at 50 ng/well in 0.1 M NaCO$_3$ (pH 9.6) at 4° C. overnight. Coated wells were blocked by 200 μl/well of 1% BSA in PBS at room temperature for 1 hour. Plates were washed three times with 200 μl/well of PBS with 0.05% Tween-20, followed by adding 100 μl of hybridoma supernatants to wells. The incubation was carried out at room temperature for 2 hours. All wells were aspirated and washed six times with 200 μl/well of PBS with 0.05% Tween-20. The plates were incubated with a 1:10,000 dilution of HRP-conjugated goat anti-mouse IgG antibody (Chemicon) for 1 hour (100 μl/well).

Then all wells were aspirated and washed six times with 200 µl/well of PBS with 0.05% Tween-20. Finally, wells were developed by 50 µl/well of tetramethyl benzidine (TMB) substrate solution (SureBlue™, KPL) and the reaction was stopped by addition of 50 µl/well of 1N HCl. The absorbance was measured at $OD_{450}$ on an ELISA reader. Of >4000 hybridoma clones screened from two fusions, 17 clones showed specificity for UDM-solublized $mIgE.Fc_L$ rather than $mIgE.Fc_S$ as determined by ELISA.

To explore the specificity of anti-CϵmX mAbs to CϵmX, the various CϵmX-specific clones were then tested for reactivity with 3 synthetic peptides, representing 3 consecutive segments of CϵmX, divided by a C residue located at residue #18 and a CHC segment at residues #39-41. Specifically, P1 peptide contains the last 4 amino acid residues of CH4 of mϵ and first 17 amino acid residues (#1-17), namely, GLAGGSAQSQRAPDRVL (SEQ ID NO:2), of CϵmX; P2 peptide contains 20 amino acid residues #19-38, namely, HSGQQQGLPRAAGGSVPHPR (SEQ ID NO:3), of CϵmX; P3 peptide contains the terminal 11 amino acid residues (#42-52), namely, GAGRADWPGPP (SEQ ID NO:4), of CϵmX and first 4 amino acid residues of the consecutive migis region, namely, the N-terminal extracellular region of the membrane anchor peptide of mϵ chain. All peptides were synthesized at Genomics Research Center, Academia Sinica (Taipei, Taiwan). The peptides were reconstituted with PBS at a concentration of 10 mg/ml. All peptides were coated on 96-well MaxiSorp plates at 500 ng/well in 0.1 M $NaCO_3$ (pH 9.6) at 4° C. overnight. Coated wells were blocked by 200 µl/well of 1% BSA in PBS at room temperature for 1 hour. Plates were washed three times with 200 µl/well of PBS with 0.05% Tween-20, followed by adding 100 µl of 1 µg/ml anti-CϵmX mAbs to wells. The incubation was carried out at room temperature for 2 hours. All wells were aspirated and washed six times with 200 □l/well of PBS with 0.05% Tween-20. The plates were incubated with a 1:10,000 dilution of HRP-conjugated goat anti-mouse IgG antibody for 1 hour. After six times with 200 µl/well of PBS with 0.05% Tween-20, 50 µl/well of TMB substrate solution was added to the wells. The reaction was stopped by addition of 50 µl/well of 1N HCl. The absorbance was measured at $OD_{450}$ on an ELISA reader. Of the many CϵmX-specific monoclonal antibodies prepared in our experiments, only 4B12 and 26H2 do not react with RADWPGPP-containing P3 peptide. 4B12 reacted with P1 peptide, and 26112 with P2 peptide. All of the other CϵmX-specific monoclonal antibodies reacted with P3 (FIG. 1). Thus, RADWPGPP (SEQ ID NO:1) is indeed a dominant immunogenic epitope. However, it is not the only immunogenic epitope.

EXAMPLE 2

4B12 and 26H2 Bind to mIgE on mIgE-Expressing B Cells

We further tested the ability of various CϵmX-specific monoclonal antibodies to bind to CHO and Ramos cell lines that were transfected with either recombinant DNA encoding $mϵ_{L(CH2-CM)}$ or $mϵ_{S(CH2-CM)}$. The two transfected CHO cell lines respectively produced $mIgE.Fc_L$ or $mIgE.Fc_S$, both of which did not form complete B cell receptor with coreceptors such as Igα and Igβ, because the CHO cells did not express those proteins. The transfected two Ramos cell lines respectively produced $mIgE.Fc_L$ or $mIgE.Fc_S$, both of which form complexes with their native coreceptors. To investigate the binding of anti-CϵmX mAbs to native CϵmX, CHO or Ramos cells expressing $mIgE.Fc_L$ or $mIgE.Fc_S$ were resuspended in FACS buffer [PBS, 1% FBS, 0.1% sodium azide, and 2 mM EDTA (pH 8.0)] at a cell density of $10^7$ cells/ml. $10^6$ cells were then incubated for 30 min on ice with 100 µl of hybridoma supernatants, followed by washing with FACS buffer. Bound antibodies were detected by incubation for 30 minutes on ice with FITC-labeled rabbit F(ab')$_2$ fragment specific for mouse IgG (AbD Secrotec), followed by washing twice with FACS buffer prior to analysis. Flow cytometry experiments were performed using a FACSCanto II flow cytometer (BD Bioscience) and analyzed using FCSExpress software (De Novo Software). All CϵmX-specific monoclonal antibodies were found not to bind to CHO and Ramos cells expressing $mIgE.Fc_S$. All CϵmX-specific monoclonal antibodies were found to bind to CHO cells expressing $mIgE_L$. However, only 4B12 and 26H2 could bind to Ramos cells expressing $mIgE.Fc_L$, while all other CϵmX-specific monoclonal antibodies could not bind to Ramos cells expressing $mIgE.Fc_L$ (FIG. 2).

EXAMPLE 3

4B12 and 26H2 Induce Antibody-Dependent Cellular Cytotoxicity Against mIgE-Expressing B Cells To investigate the ADCC activity of chimeric anti-CϵmX mAbs, we used peripheral blood mononuclear cells (PBMCs) as effector cells to target $mIgE.Fc_L$-expressing Ramos cells. PBMCs were purified from buffy coats of healthy donors (Taiwan Blood Service Foundation) by centrifugation over a Ficoll-Paque Plus (GE Healthcare) density gradient and cryo-preserved in 90% FBS/10% DMSO (Hybri-Max™; Sigma-Aldrich). Prior to use, PBMCs were thawed and cultured at $2\times10^6$ cells/ml overnight in IMDM medium (Invitrogen) supplemented with 10% heat-inactivated FBS and 1% penicillin-streptomycin mixture. To identify target cells in coculture with PBMCs, $mIgE.Fc_L$-expressing Ramos cells were labeled with 2.5 µM 5-(and -6)-carboxyfluorescein diacetate, succinimidyl ester (CFDA, SE; Invitrogen) in 0.1% BSA/PBS for 10 min at 37° C., After three washes with cold RPMI medium (Invitrogen) containing 10% FBS, cells were adjusted to $10^5$ cells/ml. For effector-target (E/T) ratio titrations, 20,000 labeled cells in 200 µl of complete RPMI medium were coated with antibodies at 1 µg/ml for 30 min at 37° C., and then combined with an equal volume of PBMCs at multiple E/T ratios from 50 to 3.125. For antibody titrations, 20,000 labeled cells in 200 µl of complete RPMI medium were opsonized with antibody at various concentrations (1000~0.01 ng/ml) for 30 minutes at 37° C., and then combined with PBMCs at an E/T ratio of 25:1. To measure antibody-independent killing, labeled target cells were also incubated with PBMCs in the absence of antibodies at given E/T ratios. At the end of 24-hour incubation, dead cells were stained with 2.5 µg/ml 7-amino actinomycin (7-AAD; Invitrogen) for 15 min on ice. Cells were analyzed on a Becton Dickinson FACSCanto II flow cytometer. Living target cells were defined as the percentage of CFSE-positive/7-AAD-negative cells on dot-plot analyses. The percentage of cells killed at a given E/T ratio was calculated according the following formula: 100×[(% of living target cells in the antibody-independent control−% of living target cells in the sample)/% of living target cells in the antibody-independent control]. The ADCC activity of c4B12, c26H2 and omalizumab was observed at multiple E/T ratios. At an E/T ratio of 50, c4B 12, c26H2 and omalizumab gave up to 60% specific lysis; in contrast, ca20 was less active and gave only 10~20% specific lysis (FIG. 3A). Besides, significant ADCC was observed when the concentration of c4B12 and c26H2 was higher than 0.01 μg/ml. At the maximum dose of 10 μg/ml, specific lysis of target cells by c4B12 and c26H2 ranged from 80% to 90%, while ca20 gave up to 50% specific lysis (FIG. 3B). The positive control rituximab, which directed to CD20, and omalizumab effectively induced ADCC at multiple E/T ratios and in dose-responsive manner. Thus, we concluded that c4B 12 and c26H2 are more potent anti-CεmX mAbs than ca20 in mediating ADCC and could efficiently recruit effector cells to target mIgE-expressing B cells in vivo.

EXAMPLE 4

Chimeric Anti-CεmX mAbs Induce Apoptosis of Membrane-Bound IgE.Fc$_L$-Expressing Ramos Cells To detect phosphatidylserine (PS) exposure, mIgE.Fc$_L$-expressing Ramos cells (5×10$^5$ cell/ml) were incubated with chimeric anti-CεmX mAbs, omalizumab or control antibodies at indicated concentrations in complete culture medium for 1 hour at 37° C. Cells were then treated with goat F(ab')$_2$ fragment specific for the Fc fragment of human IgG (Jackson ImmunoResearch Laboratories Inc.) at a concentration of 10 μg/ml and further incubated for 24 hours at 37° C. The detection of phosphatidylserine (PS) exposure was assessed by staining cells in 200 μl of Annexin buffer [10 mM HEPES/NaOH (pH 7.4), 140 mM NaCl, 5 mM CaCl$_2$] containing fluorescein isothiocyanate (FITC)-labeled Annexin V (BioVision), diluted 1/200, and 2.5 μg/ml propidium iodide (PI, Sigma-Aldrich) for 15 min in dark at room temperature. Cells were analyzed on a FACSCanto II flow cytometer. Apoptotic cells were defined as the percentage of Annexin V-positive/PI-negative cells on dot-plot analyses. Approximately 80% of mIgE.Fc$_L$-expressing Ramos cells were dead through apoptosis by increasing concentration of c4B 12, c26H2, or omalizumab, but not ca20, with maximal induction at 1 μg/ml (FIG. 4A).

For detection of apoptotic nuclei, mIgE.Fc$_L$-expressing Ramos cells (5×10$^5$ cell/ml) were incubated with chimeric anti-CεmX mAbs, omalizumab or control antibodies at a concentration of 1 μg/ml in complete culture medium for 1 hour at 37° C. Cells were then treated with goat F(ab')$_2$ fragment specific for the Fc fragment of human IgG at a final concentration of 10 μg/ml and further incubated for 48 hours at 37° C. 5×10$^5$ cells were incubated in 0.5 ml of propidium iodide (PI)/Triton solution (0.1% sodium citrate, 0.1% Triton X-100, 15 μg/ml PI, and 100 μg/ml RNase A in PBS; all from Sigma-Aldrich) for one hour in dark on ice. PI fluorescence was determined on a FACSCanto II flow cytometer. The DNA content of intact of nuclei was recorded on a linear scale. Apoptotic nuclei containing hypodiploid DNA emitting fluorescence in channels below the G$_0$/G$_1$ peak were enumerated as a percentage of the total population. A significant increase in cell population with hypodiploid DNA was observed in c4B 12, c26H2, or omalizumab-treated mIgE.Fc$_L$-expressing Ramos cells (FIG. 4B).

For detection of caspase 3 and poly(ADP-ribose) polymerase (PARP) cleavage, mIgE.Fc$_L$-expressing Ramos cells cells (5×10$^5$ cell/ml) were incubated with chimeric anti-CεmX mAbs, omalizumab or control antibodies at a concentration of 1 μg/ml in complete culture medium for 1 hour at 37° C. Cells were then treated with goat F(ab')$_2$ fragment specific for the Fc fragment of human IgG at a final concentration of 10 μg/ml and further incubated for 24 hours at 37° C. 5×10$^6$ cells were washed in ice-cold PBS and resuspended in 100 μl of ice-cold modified RIPA lysis buffer [20 mM Tris (pH 7.4), 150 mM NaCl, 1% Triton-X 100, 0.5% deoxycholate, 0.1% sodium dodecyl sulfate (SDS), 5 mM EDTA, and protease inhibitor (Sigma-Aldrich)]. The lysates were incubated for 20 min on ice. Samples were centrifuged for 20 min at 16000×g and 4° C. The supernatants were transferred to a fresh 1.5 ml tube and stored at −80° C. The amount of protein in each clarified lysate was quantified using the Protein DC assay (Bio-Rad Laboratories) according manufacturer's suggestions. Each sample was normalized for total protein content and was subjected to SDS-polyacrylamide gel electrophoresis (SDS-PAGE) followed by transfer to PVDF membranes (GE Healthcare). Rabbit polyclonal antibodies to caspase-3 and PARP were obtained from Cell Signaling Technology and were used at 1:500 dilutions. HRP-conjugated goat anti-rabbit IgG secondary antibody (Sigma-Aldrich) was used at 1:10,000 dilutions. Membranes were developed with an ECL reagent (Immobilon™ Western; Millipore). Equivalent protein loading was verified by probing the blot with an antibody to β-actin (Sigma-Aldrich). 24 hours after mIgE.Fc$_L$-expressing Ramos cells were treated by c4B 12, c26H2 and omalizumab, rather than ca20, cleavage of caspase-3 into M$_r$, 19- and 17-kDa fragments was evident. Besides, the cleavage of PARP was detectable in c4B12-, c26H2-, and omalizumab-treated mIgE.Fc$_L$-expressing Ramos cells using an antibody recognized the M$_r$, 116 kDa intact PARP and the M$_r$, 89 kDa cleavage product (FIG. 4C).

BRIEF DESCRIPTION OF THE FIGURES

FIG. 1 shows the three synthetic peptides representing the consecutive segments of CεmX and the reactivities of various anti-CεmX mAbs with those peptides. The amino acid residues of the CεmX domain are shown in bold face. CH4-migis: SEQ ID NO:11; P1: SEQ ID NO:12; P2: SEQ ID NO:3; P4: SEQ ID NO:13.

FIG. 5 shows the amino acid sequence alignment of the V$_L$ and V$_H$ of parental mouse 4B 12, the chosen human germ-line templates KV2 and HV4 for V$_L$ and V$_H$, respectively, and the humanized 4B12 (hu4B12), labeled as "Replace" in the alignments. This hu4B12 has the same binding affinity to CεmX recombinant proteins and to mIgE.Fc$_L$-expressing Ramos cells as chimeric 4B12 (c4B12). 4B12 Light chain: SEQ ID NO:5; 4B12 Heavy chain: SEQ ID NO:8; KV2 Light chain: SEQ ID NO:6; HV4 Heavy chain: SEQ ID NO:9; Hu4B12 (Replace) Light chain: SEQ ID NO:7; Hu4B12 (Replace) Heavy chain: SEQ ID NO:10.

REFERENCES CITED

Related Patent Documents

Figure 2:
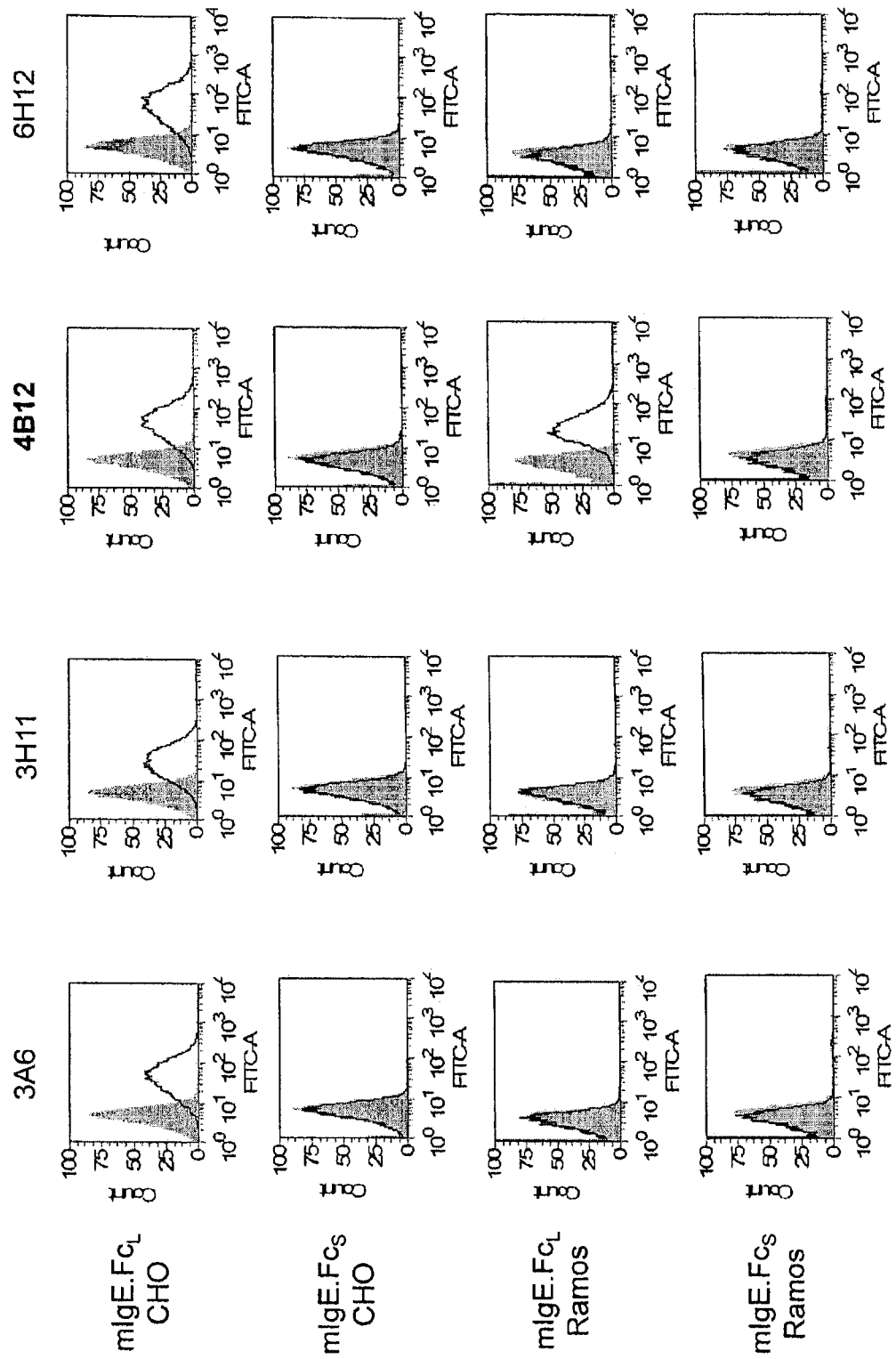
FIG. 2 shows the binding of various anti-CεmX mAbs to CHO or Ramos cell lines that express mIgE.Fc$_L$ or mIgE.Fc$_S$.
Figure 2:
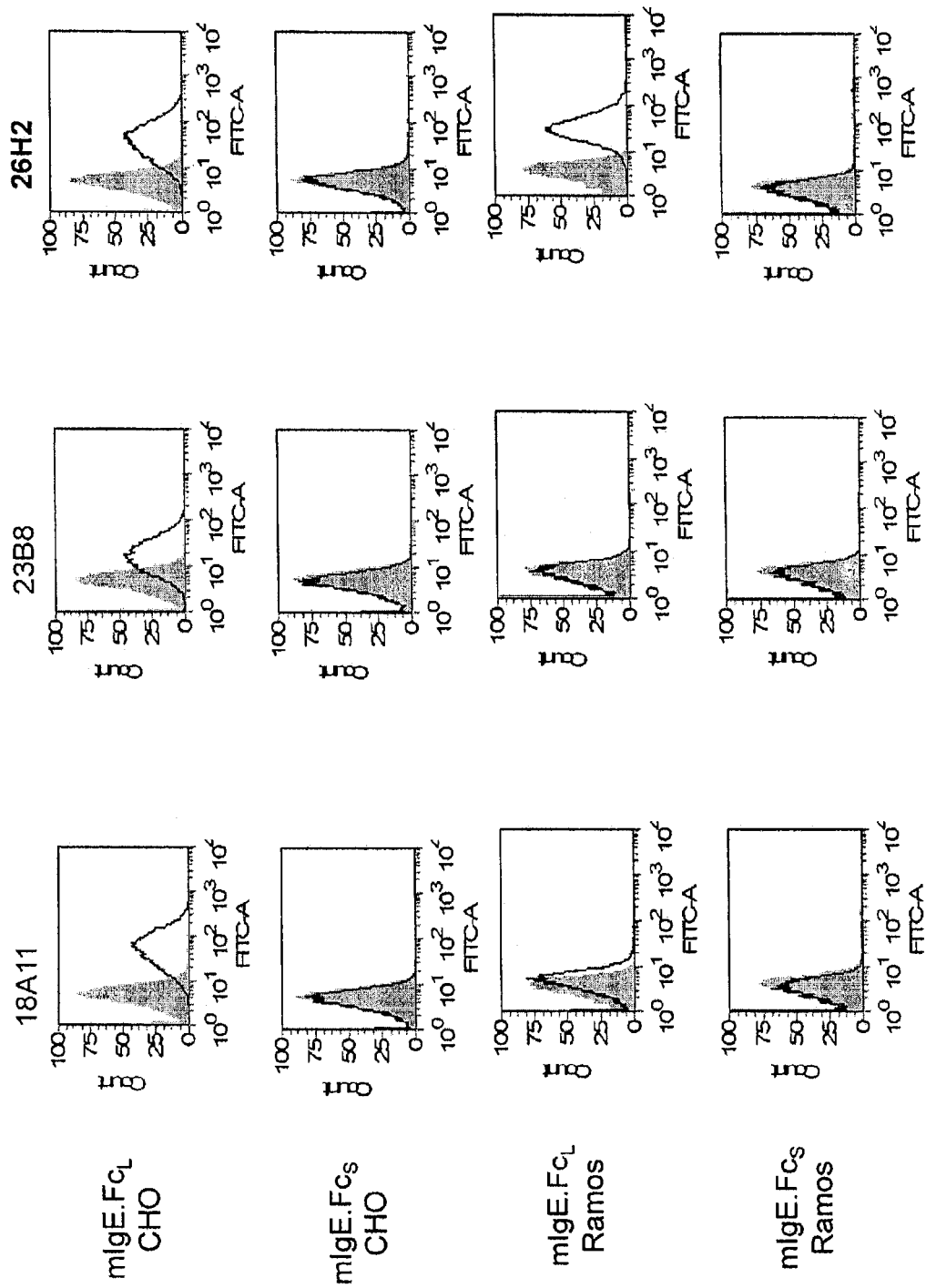
Figure 3A:
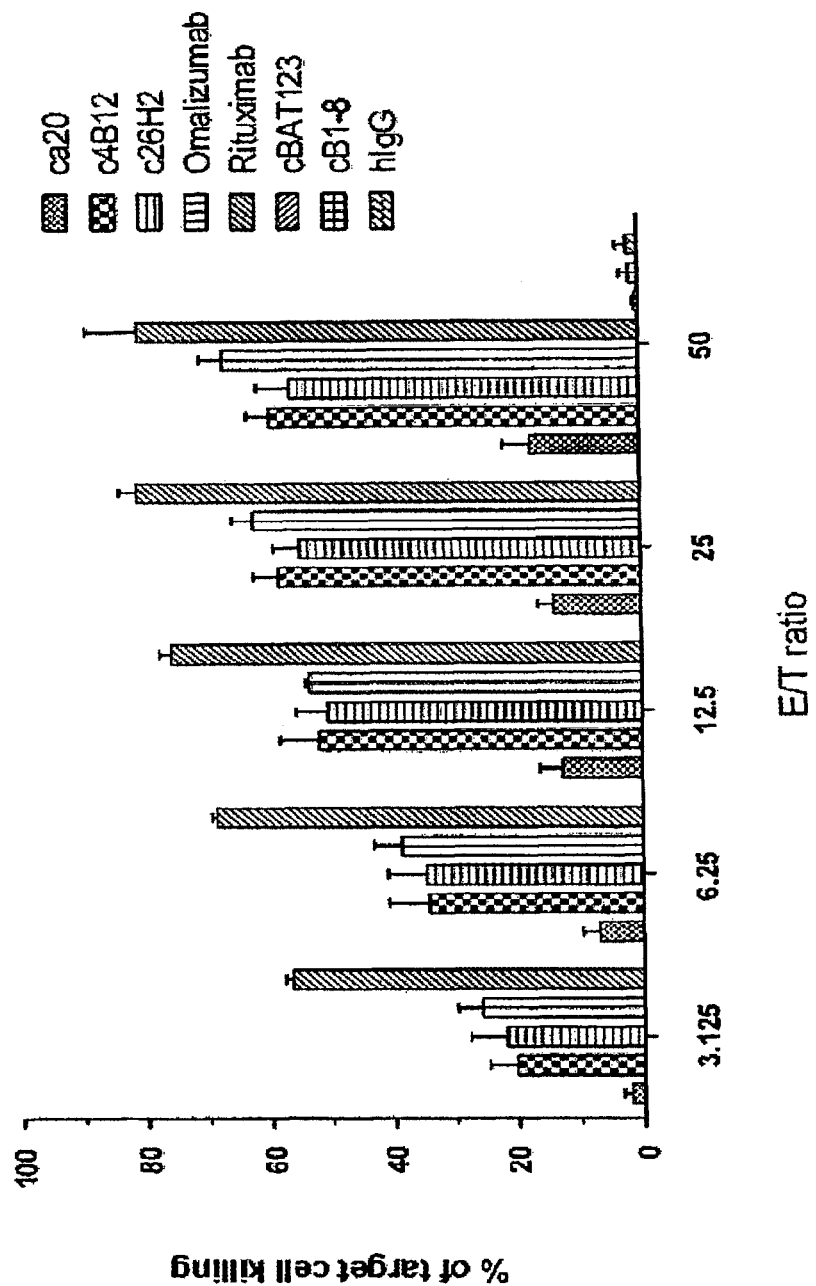
FIG. 3A shows that chimeric c4B12 and c26H2 induce ADCC against mIgE.Fc$_L$-expressing Ramos cells at multiple E/T ratios.
Figure 3B:
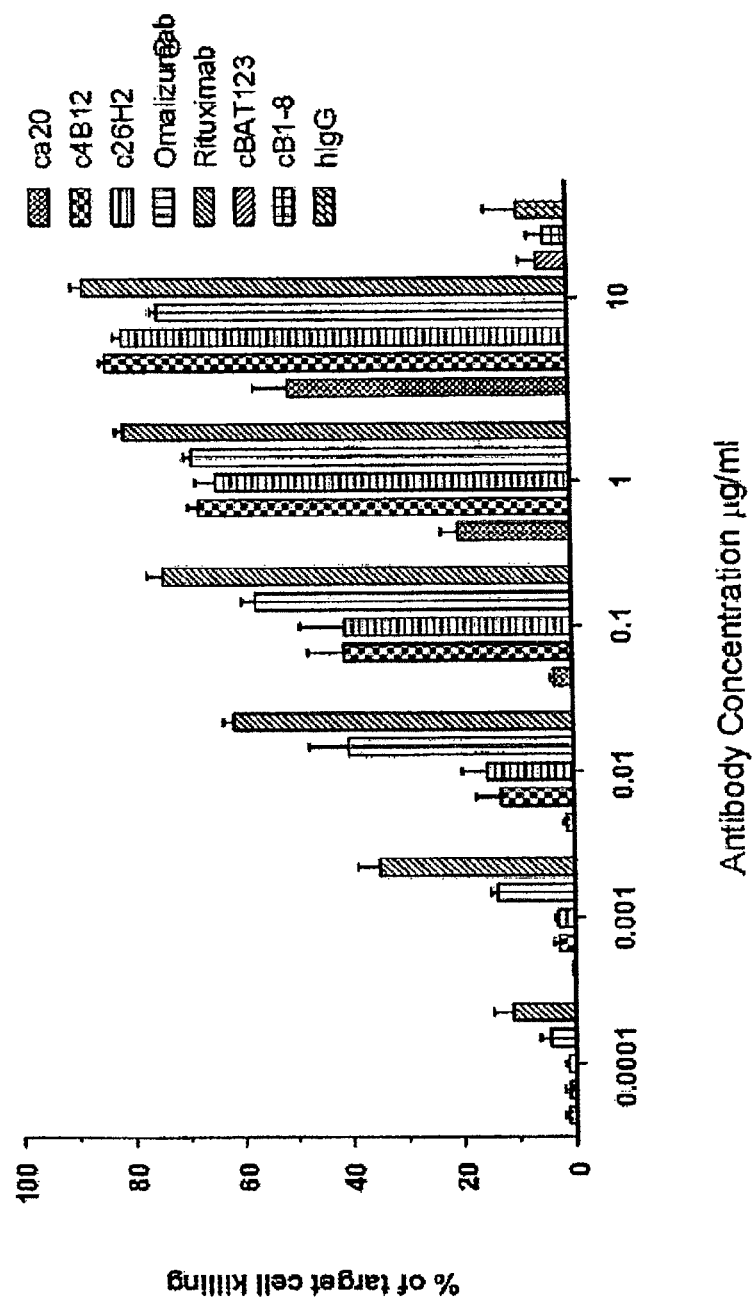
FIG. 3B shows that chimeric c4B12 and c26H2 induce ADCC against mIgE.Fc$_L$-expressing Ramos cells in a dose-responsive manner.
Figure 4A:
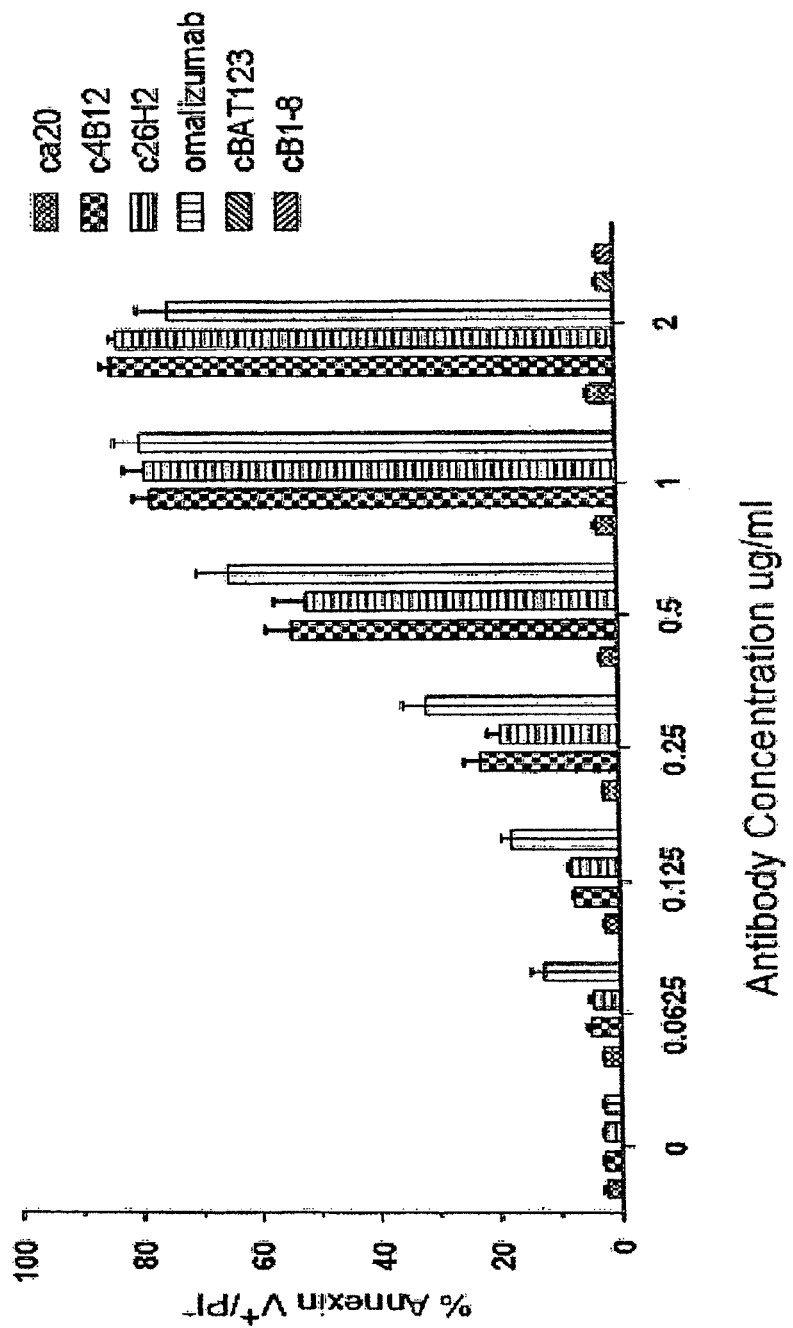
FIG. 4A shows that PS exposure induced by chimeric c4B12 and c26H2 in mIgE.Fc$_L$-expressing Ramos cells is does-dependent.
Figure 4B:
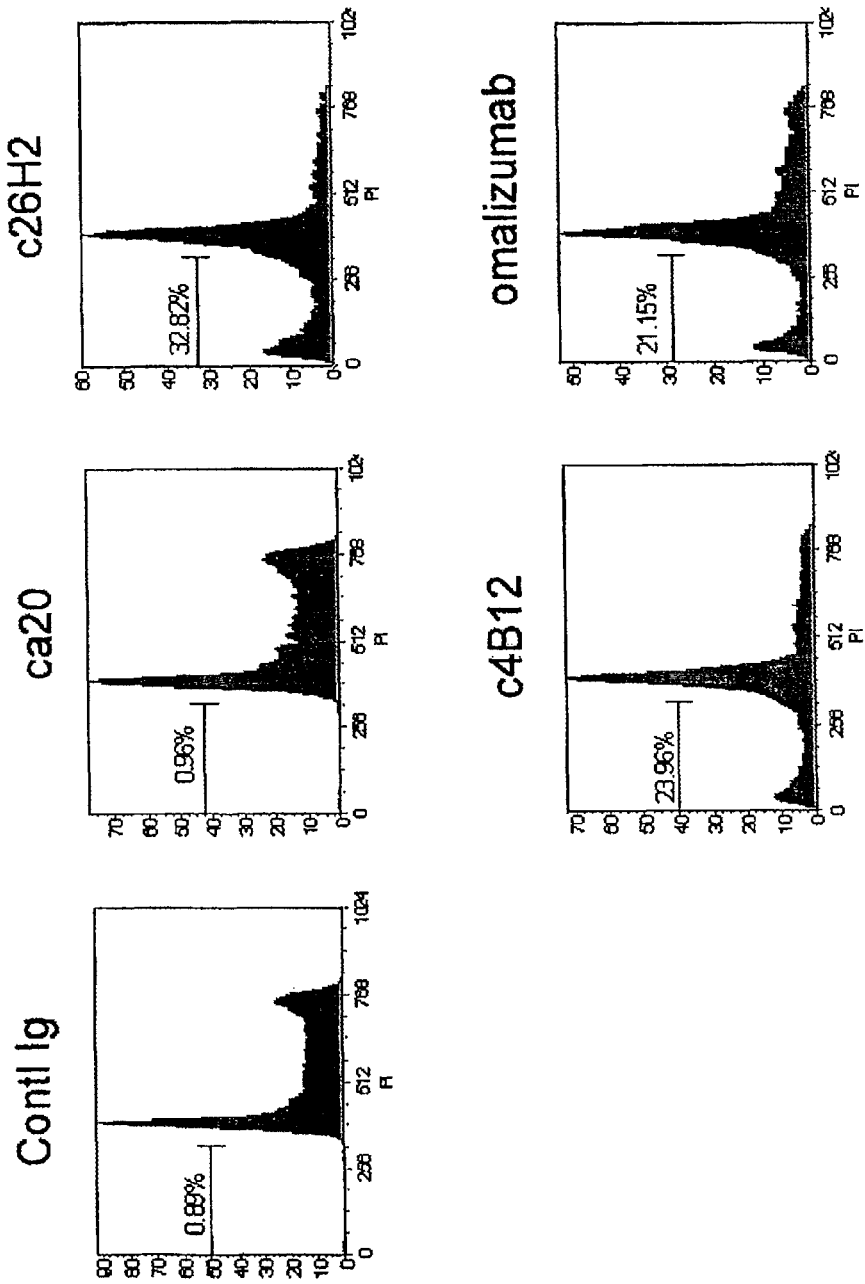
FIG. 4B shows that apoptotic nuclei were observed in chimeric c4B 12- and c26H2-treated mIgE.Fc$_L$-expressing Ramos cells.
Figure 4C:
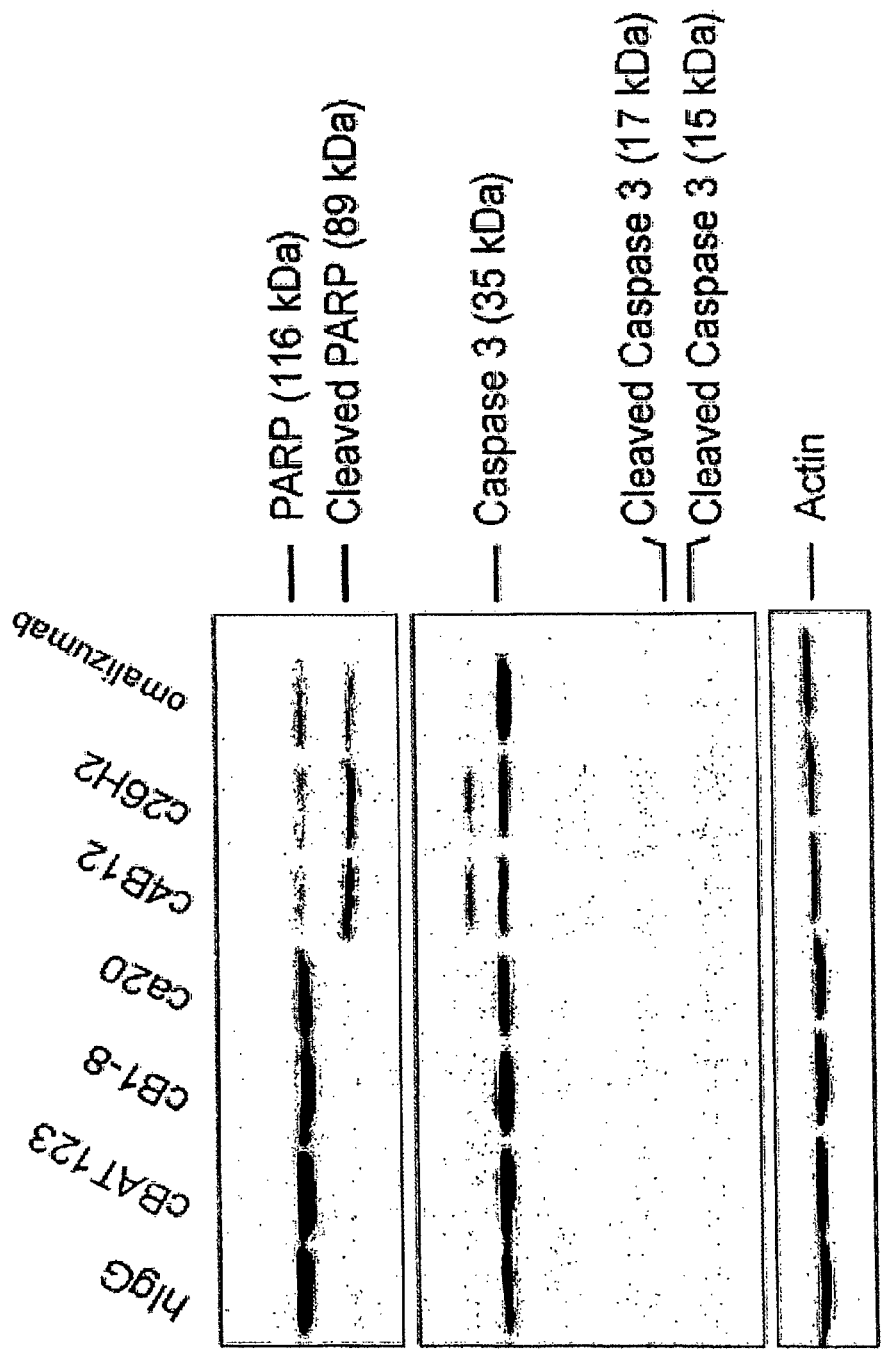
FIG. 4C shows that the cleavage of caspase 3 and PARP were observed in chimeric c4B 12- and c26H2-treated mIgE.Fc$_L$-expressing Ramos cells.

U.S. Pat. No. 5,091,313 February 1992 Chang
U.S. Pat. No. 5,254,671 October 1993 Chang
U.S. Pat. No. 5,260,416 November 1993 Chang
U.S. Pat. No. 5,274,075 December 1993 Chang U.S. Pat. No. 5,292,867 March 1994 Chang
U.S. Pat. No. 5,342,924 August 1994 Chang
US2009/0010924A1 Wu Other References Davis F M, Gossett L A, Chang T W (1991) An epitope on membrane-bound but not secreted IgE: implications in isotype-specific regulation. Bio/Technology 9: 53-56.

Peng C, Davis F M, Sun L K, Liou R S, Kim Y W, Chang T W (1992) A new isoform of human membrane-bound IgE. J Immunol 148: 129-136.

Chen, H. Y., Liu, F. T., Hou, C. M. H., Huang, J. S. W., Sharma, B. B., and Chang, T. W. (2002) Monoclonal antibodies against CεmX domain in human membrane-bound IgE and their potential on targeting IgE-expressing B cells. Int. Archives Allergy & Immunol. 128, 315-324.

What is claimed:

1. A method of inducing an immune response, comprising: administering to a human subject in need thereof an effective amount of an immunogen selected from the group consisting of GLAGGSAQSQRAPDRVL (SEQ ID NO:2) and HSGQQQGLPRAAGGSVPHPR (SEQ ID NO:3); and an adjuvant.

2. The method of claim 1, wherein the immunogen is GLAGGSAQSQRAPDRVL (SEQ ID NO:2).

3. The method of claim 1, wherein the immunogen is HSGQQQGLPRAAGGSVPHPR (SEQ ID NO:3).

4. The method of claim 2, wherein the subject has an IgE-mediated disease.

5. The method of claim 4, wherein the IgE-mediated disease is cold-induced urticaria, chronic urticaria, cholinergic urticarial, chronic rhinosinusitis, systemic mastocytosis, cutaneous mastocytosis, allergic bronchopulmonary aspergillosis, recurrent idiopathic angioedema, interstitial cystitis, or eosinophil-associated gastrointestinal disorders.

6. The method of claim 4, wherein the IgE-mediated disease is an allergic disease.

7. The method of claim 6, wherein the allergic disease is allergic asthma, allergic rhinitis, or atopic dermatitis.

8. The method of claim 2, wherein the immune response is an antibody response in which production of antibodies specific to GLAGGSAQSQRAPDRVL (SEQ ID NO:2) is induced.

9. The method of claim 8, wherein the antibodies are capable of binding to membrane-bound IgE on B lymphocytes and inducing apoptosis of the B lymphocytes.

10. The method of claim 3, wherein the subject has an IgE-mediated disease.

11. The method of claim 10, wherein the IgE-mediated disease is cold-induced urticaria, chronic urticaria, cholinergic urticarial, chronic rhinosinusitis, systemic mastocytosis, cutaneous mastocytosis, allergic bronchopulmonary aspergillosis, recurrent idiopathic angioedema, interstitial cystitis, or eosinophil-associated gastrointestinal disorders.

12. The method of claim 10, wherein the IgE-mediated disease is an allergic disease.

13. The method of claim 12, wherein the allergic disease is allergic asthma, allergic rhinitis, or atopic dermatitis.

14. The method of claim 3, wherein the immune response is an antibody response in which production of antibodies specific to HSGQQQGLPRAAGGSVPHPR (SEQ ID NO:3) is induced.

15. The method of claim 14, wherein the antibodies are capable of binding to membrane-bound IgE on B lymphocytes and inducing apoptosis of the B lymphocytes.

* * * * *

UNITED STATES PATENT AND TRADEMARK OFFICE
CERTIFICATE OF CORRECTION

PATENT NO.        : 8,974,794 B2
APPLICATION NO.   : 14/254453
DATED             : March 10, 2015
INVENTOR(S)       : Tse Wen Chang et al.

Page 1 of 1

It is certified that error appears in the above-identified patent and that said Letters Patent is hereby corrected as shown below:

On the Title page of the patent, in the Abstract (57), before the word "effectively", please delete the word "bind".

Signed and Sealed this
Fourteenth Day of July, 2015

Michelle K. Lee
*Director of the United States Patent and Trademark Office*

SEQUENCE LISTING

```
<160> NUMBER OF SEQ ID NOS: 13

<210> SEQ ID NO 1
<211> LENGTH: 8
<212> TYPE: PRT
<213> ORGANISM: Homo sapiens
<220> FEATURE:
<221> NAME/KEY: DOMAIN
<222> LOCATION: (1)..(8)
<223> OTHER INFORMATION: residues 45-52 from the C-terminal end of the
      C(epsilon)mX domain located between the CH4 domain and the
      C-terminal membrane-anchoring segment of human membrane-bound
      (epsilon) chain

<400> SEQUENCE: 1

Arg Ala Asp Trp Pro Gly Pro Pro
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic sequence
<220> FEATURE:
<221> NAME/KEY: PEPTIDE
<222> LOCATION: (1)..(17)

<400> SEQUENCE: 2

Gly Leu Ala Gly Gly Ser Ala Gln Ser Gln Arg Ala Pro Asp Arg Val
1               5                   10                  15

Leu

<210> SEQ ID NO 3
<211> LENGTH: 20
<212> TYPE: PRT
<213> ORGANISM: Artificial Sequence
<220> FEATURE:
<223> OTHER INFORMATION: Synthetic sequence
<220> FEATURE:
<221> NAME/KEY: PEPTIDE
<222> LOCATION: (1)..(20)

<400> SEQUENCE: 3

His Ser Gly Gln Gln Gln Gly Leu Pro Arg Ala Ala Gly Gly Ser Val
1               5                   10                  15

Pro His Pro Arg
            20

<210> SEQ ID NO 4
<211> LENGTH: 11
<212> TYPE: PRT
<213> ORGANISM: Artificial Sequence
<220> FEATURE:
<223> OTHER INFORMATION: Synthetic sequence
<220> FEATURE:
<221> NAME/KEY: PEPTIDE
<222> LOCATION: (1)..(11)
```

<400> SEQUENCE: 4

Gly Ala Gly Arg Ala Asp Trp Pro Gly Pro Pro
1               5                   10

<210> SEQ ID NO 5
<211> LENGTH: 113
<212> TYPE: PRT
<213> ORGANISM: Mus musculus

<400> SEQUENCE: 5

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Phe Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

Arg

<210> SEQ ID NO 6
<211> LENGTH: 113
<212> TYPE: PRT
<213> ORGANISM: Homo sapiens

<400> SEQUENCE: 6

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ile Gln Leu Pro Pro Thr Phe Gly Gly Gly Thr Lys Val Glu Ile Lys
            100                 105                 110

Arg

<210> SEQ ID NO 7
<211> LENGTH: 113
<212> TYPE: PRT
<213> ORGANISM: Artificial Sequence
<220> FEATURE:
<223> OTHER INFORMATION: humanized mouse 4B12 light chain variable
      region

```
<220> FEATURE:
<221> NAME/KEY: DOMAIN
<222> LOCATION: (1)..(113)
<223> OTHER INFORMATION: humanized mouse 4B12 light chain variable
      region

<400> SEQUENCE: 7

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Pro Thr Phe Gly Gly Gly Thr Lys Val Glu Ile Lys
            100                 105                 110

Arg

<210> SEQ ID NO 8
<211> LENGTH: 117
<212> TYPE: PRT
<213> ORGANISM: Mus musculus

<400> SEQUENCE: 8

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Ser Ile Ser Tyr Ser Gly Ile Thr Gly Tyr Asn Pro Ser Leu
    50                  55                  60

Lys Ser Arg Ile Ser Val Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Met Gly Tyr Asp Gly Leu Ala Tyr Trp Gly His Gly Thr Thr
            100                 105                 110

Val Thr Val Ser Ala
        115

<210> SEQ ID NO 9
<211> LENGTH: 110
<212> TYPE: PRT
<213> ORGANISM: Homo sapiens

<400> SEQUENCE: 9

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45
```

```
Met Ile Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Tyr Trp Gly Gln Gly Thr Leu Val Thr Val Ser Ser
            100                 105                 110
```

<210> SEQ ID NO 10
<211> LENGTH: 117
<212> TYPE: PRT
<213> ORGANISM: Artificial Sequence
<220> FEATURE:
<223> OTHER INFORMATION: humanized mouse 4B12 heavy chain
<220> FEATURE:
<221> NAME/KEY: DOMAIN
<222> LOCATION: (1)..(117)
<223> OTHER INFORMATION: humanized mouse 4B12 heavy chain region

<400> SEQUENCE: 10

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Asp
                20                  25                  30

Tyr Ala Trp Asn Trp Ile Arg Gln Pro Pro Gly Lys Gly Leu Glu Trp
            35                  40                  45

Met Ile Ser Ile Ser Tyr Ser Gly Ile Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Met Gly Tyr Asp Gly Leu Ala Tyr Trp Gly Gln Gly Thr Leu
            100                 105                 110

Val Thr Val Ser Ser
        115
```

<210> SEQ ID NO 11
<211> LENGTH: 60
<212> TYPE: PRT
<213> ORGANISM: Artificial Sequence
<220> FEATURE:
<223> OTHER INFORMATION: Synthetic Polypeptide

<400> SEQUENCE: 11

```
Ser Val Asn Pro Gly Leu Ala Gly Gly Ser Ala Gln Ser Gln Arg Ala
1               5                   10                  15

Pro Asp Arg Val Leu Cys His Ser Gly Gln Gln Gln Gly Leu Pro Arg
                20                  25                  30

Ala Ala Gly Gly Ser Val Pro His Pro Arg Cys His Cys Gly Ala Gly
            35                  40                  45

Arg Ala Asp Trp Pro Gly Pro Pro Glu Leu Asp Val
        50                  55                  60
```

<210> SEQ ID NO 12
<211> LENGTH: 21
<212> TYPE: PRT
<213> ORGANISM: Artificial Sequence
<220> FEATURE:
<223> OTHER INFORMATION: Synthetic Polypeptide

```
<400> SEQUENCE: 12

Ser Val Asn Pro Gly Leu Ala Gly Gly Ser Ala Gln Ser Gln Arg Ala
1               5                   10                  15

Pro Asp Arg Val Leu
            20

<210> SEQ ID NO 13
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 13

Gly Ala Gly Arg Ala Asp Trp Pro Gly Pro Pro Glu Leu Asp Val
1               5                   10                  15
```